United States Patent
Goulter (10) Patent No.: US 7,014,635 B2
(45) Date of Patent: Mar. 21, 2006

(54) METHOD AND APPARATUS FOR PREPARING AND FITTING CONDOM CATHETERS

(76) Inventor: Victor Harold Goulter, 33 Carter Avenue, Werribee, Victoria (AU) 3030

(*) Notice: Subject to any disclaimer, the term of this patent is extended or adjusted under 35 U.S.C. 154(b) by 345 days.

(21) Appl. No.: 10/440,532

(22) Filed: May 13, 2003

(65) Prior Publication Data
US 2004/0230180 A1   Nov. 18, 2004

(51) Int. Cl.
*A61M 27/00* (2006.01)

(52) U.S. Cl. .................. 604/544; 604/346
(58) Field of Classification Search ........ 604/346–353, 604/355, 544, 174; 128/842, 844, 918; 206/69
See application file for complete search history.

(56) References Cited

U.S. PATENT DOCUMENTS

| | | | | |
|---|---|---|---|---|
| 3,282,414 A | * | 11/1966 | Penksa | 206/205 |
| 4,731,064 A | * | 3/1988 | Heyden | 604/352 |
| 4,872,463 A | * | 10/1989 | Nishizono | 128/844 |
| 4,955,971 A | * | 9/1990 | Goulter | 294/7 |
| 4,972,850 A | * | 11/1990 | Broad, Jr. | 128/844 |
| 4,987,905 A | * | 1/1991 | Broad, Jr. | 128/844 |
| 5,009,236 A | * | 4/1991 | Brothers | 600/574 |
| 5,165,422 A | * | 11/1992 | Broad, Jr. | 128/844 |
| 5,353,805 A | * | 10/1994 | Mojena | 600/574 |
| 5,437,286 A | * | 8/1995 | Stratton | 128/844 |
| 5,457,823 A | * | 10/1995 | Mojena | 4/144.2 |
| 5,606,982 A | * | 3/1997 | Piotti | 128/842 |
| 5,713,880 A | * | 2/1998 | Anderson | 604/349 |
| 5,979,448 A | * | 11/1999 | Weller et al. | 128/844 |
| 6,068,618 A | * | 5/2000 | Anderson | 604/349 |
| 6,102,043 A | * | 8/2000 | Johnson | 128/844 |
| 6,416,462 B1 | * | 7/2002 | Tovey et al. | 600/121 |
| 6,425,397 B1 | * | 7/2002 | Liehs | 128/842 |
| 2004/0176731 A1 | * | 9/2004 | Cheng et al. | 604/329 |

FOREIGN PATENT DOCUMENTS

| | | | |
|---|---|---|---|
| FR | 2 693 652 A1 | * | 1/1994 |
| FR | 2 751 869 A1 | * | 2/1998 |
| WO | WO 97/00652 | * | 1/1997 |

* cited by examiner

*Primary Examiner*—Tatyana Zalukaeva
*Assistant Examiner*—Michael G. Bogart

(57) ABSTRACT

A method and apparatus are provided for fitting a condom-style catheter onto a penis of a user. The apparatus includes two jaws moveable toward and away from each other. The jaws, in a first position, surround a first portion of the catheter and retain against surfaces of the jaws a toroidal roll formed of a rolled-up open-ended sheath portion of the catheter adjoining the first portion. The jaws are then moved outwardly to a second position relative to each other so that an opening bounded by a wall of the first portion of said catheter between the jaws is shaped and opened up sufficiently to admit placement of an end of a penis therein. The jaws can then be moved inwardly to a position in which the catheter is located on the penis and the roll can be unrolled from the jaws and along said penis.

14 Claims, 6 Drawing Sheets

METHOD AND APPARATUS FOR PREPARING AND FITTING CONDOM CATHETERS

FIELD OF THE INVENTION

The present invention is related to male incontinence devices, and in particular to apparatus for easing the process of securing a sheath portion of a condom-style catheter on a penis.

BACKGROUND

U.S. Pat. No. 5,618,277 dated Apr. 8, 1997, issued to Victor Goulter, U.S. Pat. No. 5,380,312 dated Jan. 10, 1995, issued to Victor Goulter, and U.S. Pat. No. 5,009,649, dated Apr. 23, 1991, issued to Victor Goulter and Barbara Goulter, all hereby incorporated by reference in this specification, disclose incontinence devices in the form of a condom-style catheter intended in use to be worn on a user's penis. An open-ended proximal or end portion fits over the penis, and a distal portion collects urine expelled from the penis. A non-return valve is provided between the proximal and distal portions. Such condom-style catheters are suitable for wearing during most normal social and business activities, providing many advantages including the avoidance of the skin-damaging and painful adhesives often used to keep devices in place and the likelihood of detection and/or spilling which accompanies the use of leg bags.

There is however one common problem with the Goulter catheter as well as some other multi-use external catheter devices for the management of male incontinence. This problem is the inability of some users and/or their caregivers to easily and correctly roll down the condom catheter and then fit it onto the penis. Caregivers also have to deal with the fact that their handling of the penis sometimes results in a partial erection, making less handling of the penis preferable. Also, when the condom catheter is not properly fitted on, it may tend to loosen or slip partially off later, thereby leading to the pooling of urine at the distal end of the sheath portion, with the result that the tip of the penis remains bathed in urine.

Another problem is that men who have difficulty getting the device on often choose a larger size than is desirable, which in turn leads to the device falling off.

Accordingly, one object and advantage of the present invention is to provide apparatus and a method whereby a user or care-giver can prepare and fit the catheter more quickly and easily.

A further object and advantage is to provide apparatus and a method which makes it possible to place the glans penis close up against the non-return valve, with the result that little if any urine can pool at the distal end of the sheath.

A further object and advantage is to provide means for users to prepare and apply a small-enough size condom catheter, so that it can stay on securely.

SUMMARY OF INVENTION

In a first aspect, the invention provides apparatus for fitting a condom-style catheter to a penis of a user, including at least two jaw members and movement means for moving said jaw members towards and away from each other, wherein:

said jaw members are adapted, in a first position relative to each other, to surround a first portion of said catheter and to retain against external surfaces of said jaws a toroidal roll formed of a rolled-up open-ended end portion of said catheter adjoining said first portion;

said movement means is operable by a user to move said jaw members outwardly to a second position relative to each other wherein said toroidal roll and a wall of said first portion of said catheter between said jaw members are distended to form an opening of a size and shape suitable to admit placement of an end of a penis therein; and said movement means is operable by a user to move said jaw members inwardly from said second position to a position in which said catheter is located on said penis and said toroidal roll is positioned for unrolling from said jaw members and thereafter along said penis by a user, so that said penis is located within said catheter.

Preferably, this apparatus has two said jaw members and said movement means includes two elongate members pivotally mounted to each other at a point partway along each said elongate member, each said jaw member is mounted on one of said elongate members in a position mutually opposing the other said jaw member, and a section of each elongate member on a side of the pivot opposite the jaw member thereon is adapted to serve as a handle.

The operations of firstly rolling an end portion of the catheter into a toroidal roll and secondly fitting that roll over the penis so that the catheter can simply be unrolled over the penis, can be carried out by separate pieces of apparatus. To this end, the invention provides, in a further aspect, a pair of tools for fitting a condom-style catheter to a penis of a user including a first tool for forming an open-ended portion of said catheter into a toroidal roll thereby to prepare said catheter for fitting to said penis, and a second tool as disclosed above.

However, in a preferred alternative arrangement, each said elongate member has an elongate extension and said extensions are adapted to be inserted together by a user into said end portion of said catheter and urged outwardly against an interior surface of said end portion by rotation of said elongate members about said pivot by a user, thereby to serve together as a former along which said end portion can be rolled by a user to form said toroidal roll. This arrangement allows a single device to be used firstly to roll up an end portion of the catheter into a toroidal roll and then to fit it over the end of the penis so that it can then be unrolled over the penis. One part of the device is used for rolling up the end portion of the catheter into a toroidal roll, that roll is transferred to a second part of the device and the second part is used for actual fitting to the penis.

In another aspect, the invention provides a method for fitting a condom-style catheter to a penis including the steps of:

inserting at least one elongate object into an open end of said catheter;

rolling a portion of said catheter along said object to form said portion of said catheter into a toroidal roll;

positioning a plurality of jaw members around an unrolled portion of said catheter adjacent to said toroidal roll;

further rolling said catheter over said jaw members so that said toroidal roll is retained on said jaw members and said unrolled portion of said catheter is between said jaw members;

moving said jaw members apart from each other so that an opening bounded by said toroidal roll and a wall of said unrolled portion of said catheter between said jaw members is increased in size;

placing said penis in said opening; and unrolling said toroidal roll from said jaw members and thereafter along said penis, whereby to enclose said penis in said catheter.

Preferably, the method includes the step of withdrawing the or each said elongate object from said catheter after formation of said toroidal roll and before rolling of said toroidal roll onto said jaw members.

The invention further provides apparatus for use in rolling an open-ended portion of a condom-style catheter into a toroidal roll, including a plurality of elongate arms adapted to be inserted together by a user into said portion of said catheter, means for urging said arms outwardly against an interior surface of said catheter, whereby said arms serve together as a former along which said end portion can be rolled by a user to form said toroidal roll.

In a preferred form, apparatus for use in rolling an open-ended portion of a condom-style catheter into a toroidal roll, includes two elongate arms pivotally secured to each other in generally "V" shaped arrangement with an angle between said arms being variable by pivoting, said arms being adapted to be inserted together by a user into said end portion of said catheter and urged outwardly against an interior surface of said end portion by pivoting of said arms, thereby to serve together as a former along which said end portion can be rolled by a user to form said toroidal roll.

A pair of tools for fitting a condom-style catheter to a penis of a user may include a first tool for rolling an open-ended end portion of said catheter into a toroidal roll, as disclosed above, and a second tool as disclosed above for expanding said toroidal roll sufficiently for placement thereof around said penis and releasing said catheter as preparation for unrolling of said portion of said catheter onto said penis by a user.

Other features and preferred aspects of the invention will become apparent from the following description and from the appended claims, which are explicitly made a part of this disclosure of the invention.

Preferred aspects of the invention will now be described in detail, by reference to the following diagrams.

BRIEF DESCRIPTIONS OF THE FIGURES

FIG. 4 also shows a finger and thumb of the other hand pressed against the catheter bead and sheath in the direction of arrows "E" and "F," ready to roll the sheath along the extended blades in the direction of arrows "G" and "H."

DETAILED DESCRIPTION OF PREFERRED EMBODIMENTS OF THE INVENTION

As stated above, the invention may take the form of a pair of devices usable in sequence to carry out the processes of rolling up an end portion of a condom-style catheter into a toroidal roll and then fitting that roll over a penis for subsequent unrolling over the penis. It may also take the form of a single device capable of carrying out both of these processes. Both are described below, together with the inventive method of the invention.

Figure 1:
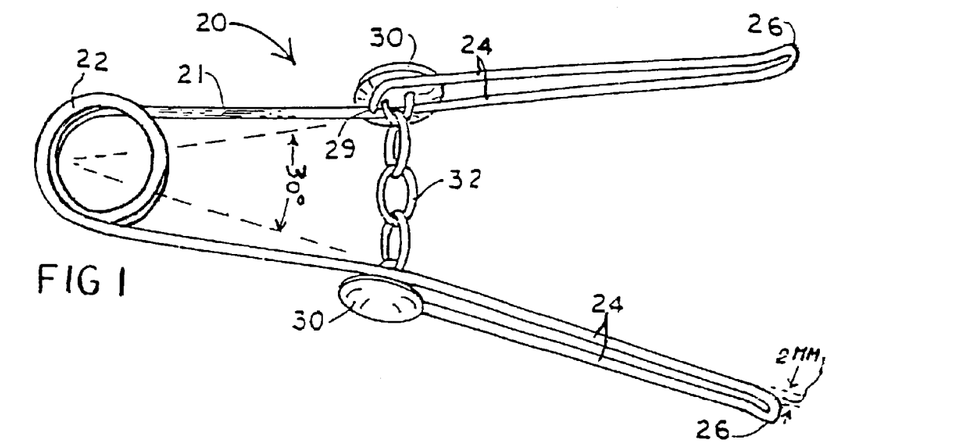
FIG. 1 is an elevated perspective view of a rolling-up device according to the invention, having two extended blades and two cupped finger-grips attached to a limit chain.
Figure 2:
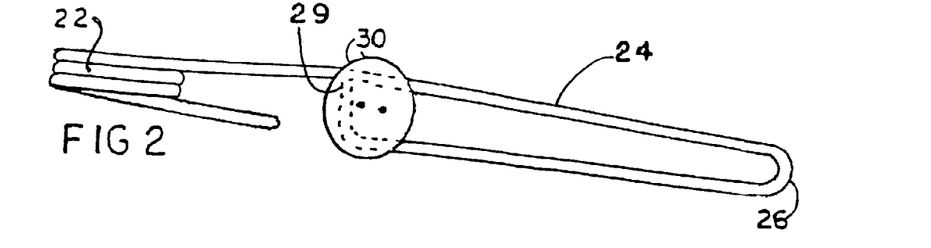
FIG. 2 is a side-perspective view of a part of the device shown in FIG. 1, showing a two-and-a-quarter coil pressure spring, one finger grip and one extended blade.
Figure 3:
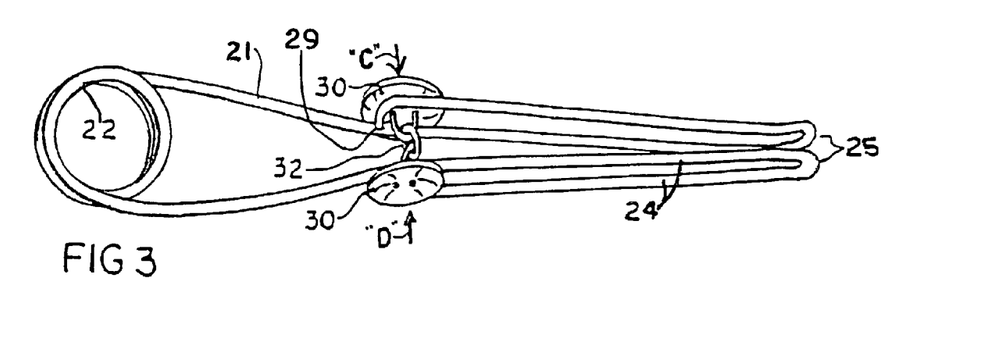
FIG. 3 is an elevated perspective view of the device shown in FIG. 1, showing the extended blades closed together when pressure is applied to the finger grips in the direction of arrows "C" and "D".
Figure 4:
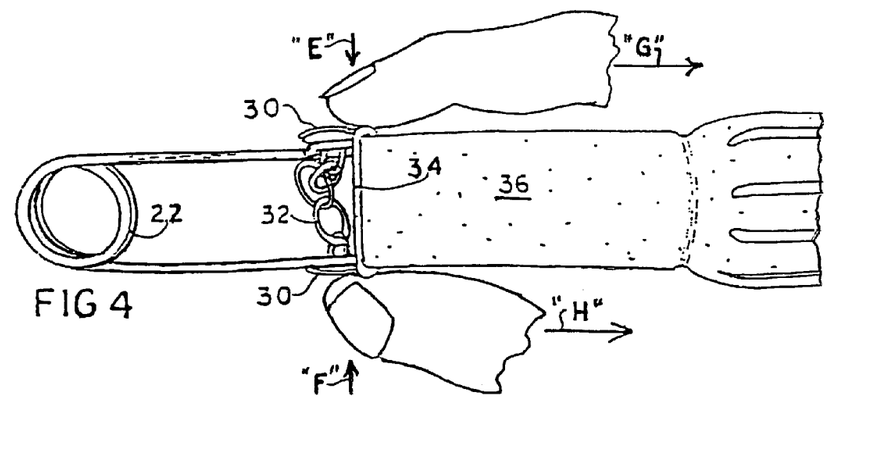
FIG. 4 is a top-perspective view of the device shown in FIG. 1 after being inserted into the open end of the sheath of a condom catheter and then having hand pressure released.

FIG. 1 shows a roll-up device 20 according to the invention. Device 20 consists of two main parts. One part is made from about 80 cm of 2.24 mm stainless steel spring wire 21, or any other suitable material.

At its central position, wire 21 is coiled into a 25 mm diameter spring 22. Spring 22 has two and a quarter coils. The remaining two extended ends of wire are of equal length and if unrestrained lie at an angle of 90 degrees to each other. (not shown)

At a position 18 cm from the center of coil 22, both wires are bent back to form two double wire extended blades 24, each having a rounded tip 26. At position 29, which is 11 cm from tip 26, the wires are bent and their ends welded or soldered to themselves as shown in FIG. 1, thus forming two enclosed double wire extension blades 24.

Tips 26 are bent outward about 2 mm as shown in FIG. 1, to improve their capacity to retain the catheter during the final stages of the roll-up process described below.

The second part of the roll-up device 20 includes two cupped finger grips 30. Grips 30 are made from stainless steel sheet (for example) and are attached to a 35 mm length of stainless steel chain 32.

The second part of the roll-up device is fitted and welded or soldered in position onto the first part by closing the angle of the double wire extended blades 24 against the resistance of spring 22 from 90 degrees apart to about 30 degrees as shown in FIG. 1. The outward spring pressure on the wire extension blades 24 is then about 1 kg.

Method of Using Roll-Up Device—FIGS. 1–5

The Method is as Follows:
a) Press inwardly on finger grips 30 in the direction of arrows "C" and "D" (FIG. 3) until blades 24 are closed together.
b) Insert both blades 24 into the open end of a catheter sheath 36 as far as they will go (FIG. 4).
c) Relax finger and thumb pressure, thus allowing blades 24 to exert outward spring pressure thereby stretching sheath 36 into a rectangular cross-sectional shape along its length.
d) Then press finger and thumb of other hand against bead 34 and sheath 36 in the direction of arrows "E" and "F."
e) Roll the sheath 36 along the extension blades 24 in the direction of arrows "G" and "H" until sheath 36 is fully rolled up.

Figures 5, 5A:
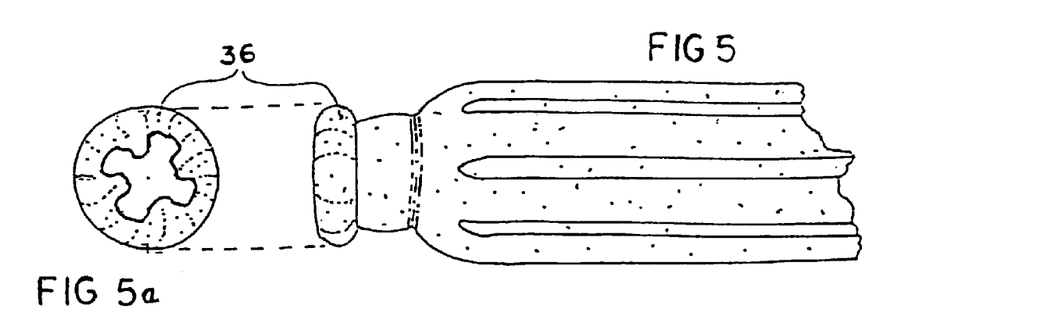
FIG. 5 is a side view of a part of the sheath shown in FIG. 4, after it has been rolled up and removed from the device.
FIG. 5a is an end view of the sheath shown in FIG. 4, after it has been rolled up and removed from the device.

FIGS. 5 and 5*a* show a side and end view of rolled-up sheath 36 with roll-up device 20 removed.

Detailed Description of Applicator Device—FIGS. 6–12

Figure 6:
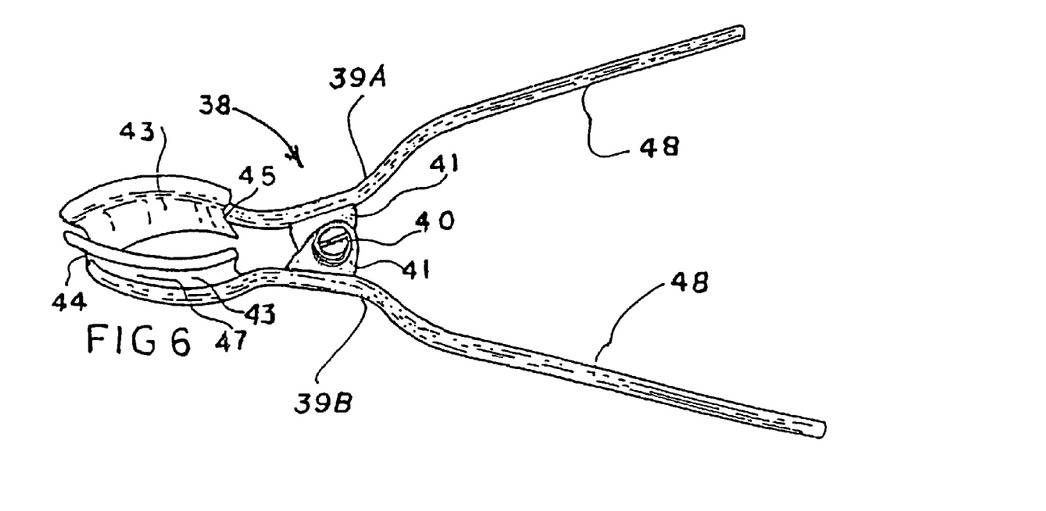
FIG. 6 is an elevated perspective view of an applicator device according to the invention with two jaws in a closed position.

FIG. 6 shows a perspective view of an APPLICATOR DEVICE 38. This device includes two opposing members 39A and 39B, which are made from about 175 mm of 4 mm or 5 mm stainless steel rod, or any other suitable material.

Figure 8:
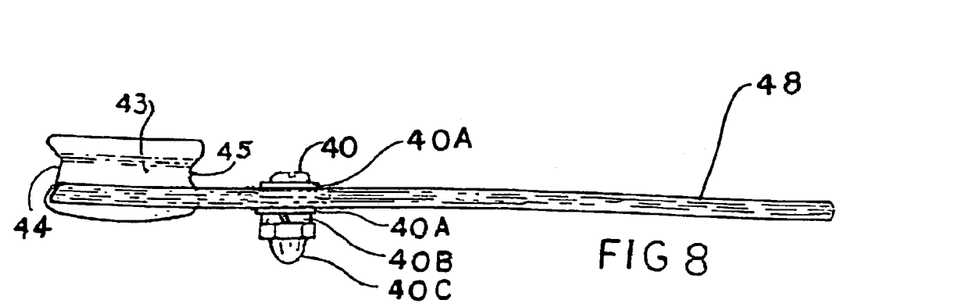
FIG. 8 is a side view of the applicator device of FIG. 6 showing one jaw with a recessed hook at each side; also an adjustable friction-applying cap nut, spring washer, flat washers, and center pivot-bolt.

Members 39A and 39B are pivoted together by a pivot bolt 40, which passes through center holes in two friction plates 41 between members 39A and 39B. One friction plate 41 is attached to each of members 39A and 39B by welding. Two flat washers 40A, one spring washer 40B and one cap nut 40C are fitted onto bolt 40. The tightness of cap nut 40C on bolt 40 determines the resistance to relative movement of members 39A and 39B, as necessary to hold the jaws together immobile during use of applicator 38.

Each member 39A and 39B has a curved jaw 43, made of stainless steel sheet or other suitable material, which is welded or soldered or otherwise permanently attached thereto at one end. Those parts of members 39A and 39B remote from jaws 43 form handles 48.

Each jaw 43 has two recessed ends 44 and 45 which form hooks. Top side 46 of each curved jaw 43 is bent outward to form a curved channel 47 between it and its respective member 39A or 39B.

Figure 7:
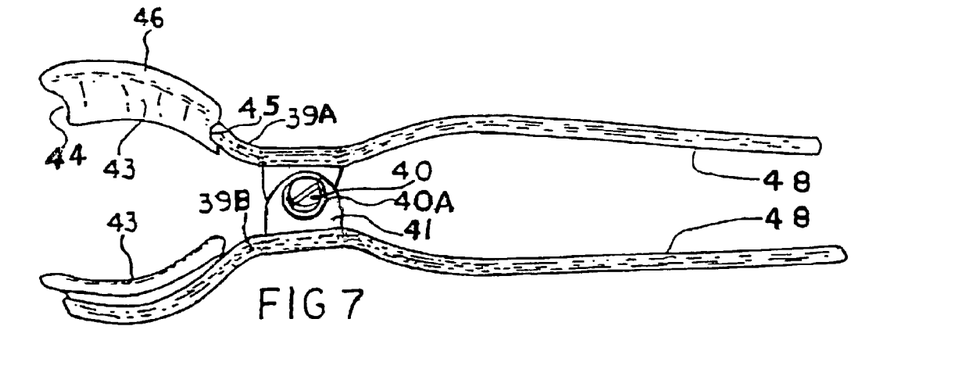
FIG. 7 is an elevated perspective view of the applicator device shown in FIG. 6 with the two jaws in an open position.

Pivot bolt 40 is positioned between the two members 39A and 39B so that when handles 48 are spread apart, i.e., opened by hand, jaws 43 will be close together, and when handles 48 are forced together by hand pressure, the jaws will spread apart with multiplied force.

Description of Operation of Applicator Device—FIGS. 9–12

Figure 9:
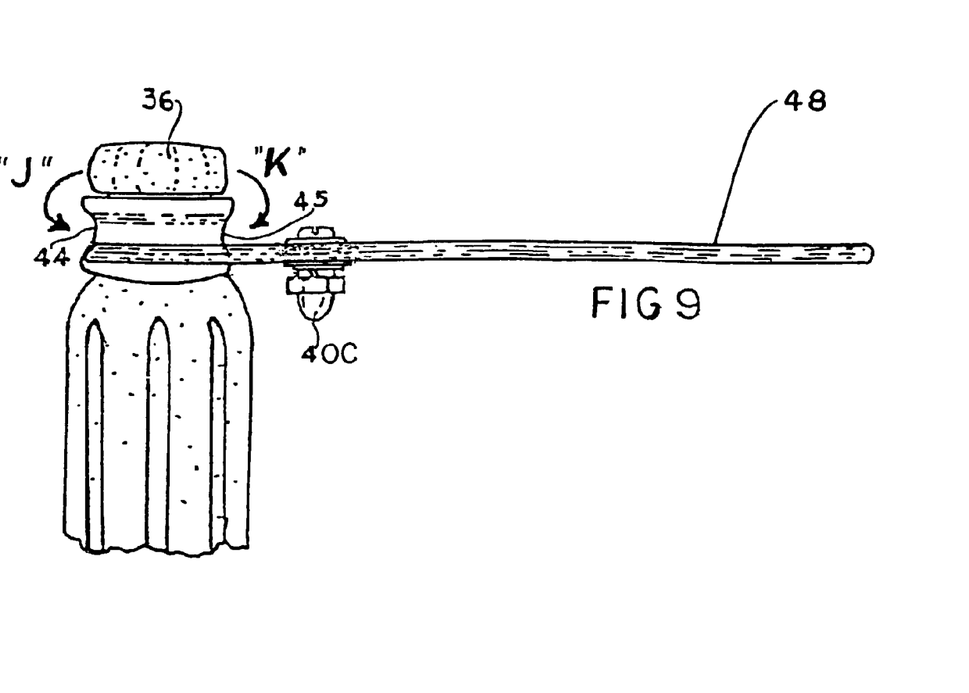
FIG. 9 is a side view of the jaws of the applicator device of FIG. 6 closed around the neck of the catheter immediately below the rolled-up sheath.

After the roll-up device 20 has been used to roll the sheath 36 up as shown in FIG. 5, the applicator jaws 43 are closed around the neck of the catheter just below the rolled-up part of the sheath 36 as shown in FIG. 9. Arrows "J" and "K," FIG. 9, indicate the direction and sequence by which the rolled-up sheath is pulled down by the fingers, first onto recessed jaw end 44 near "J" arrow, where it can be held in place by the thumb. Then the rolled-up sheath is stretched onto recessed jaw end 45 near arrow "K." The remainder of the rolled-up part of sheath 36 will then automatically accommodate itself into both curved channels 47; see FIG. 10.

Figures 10, 11:
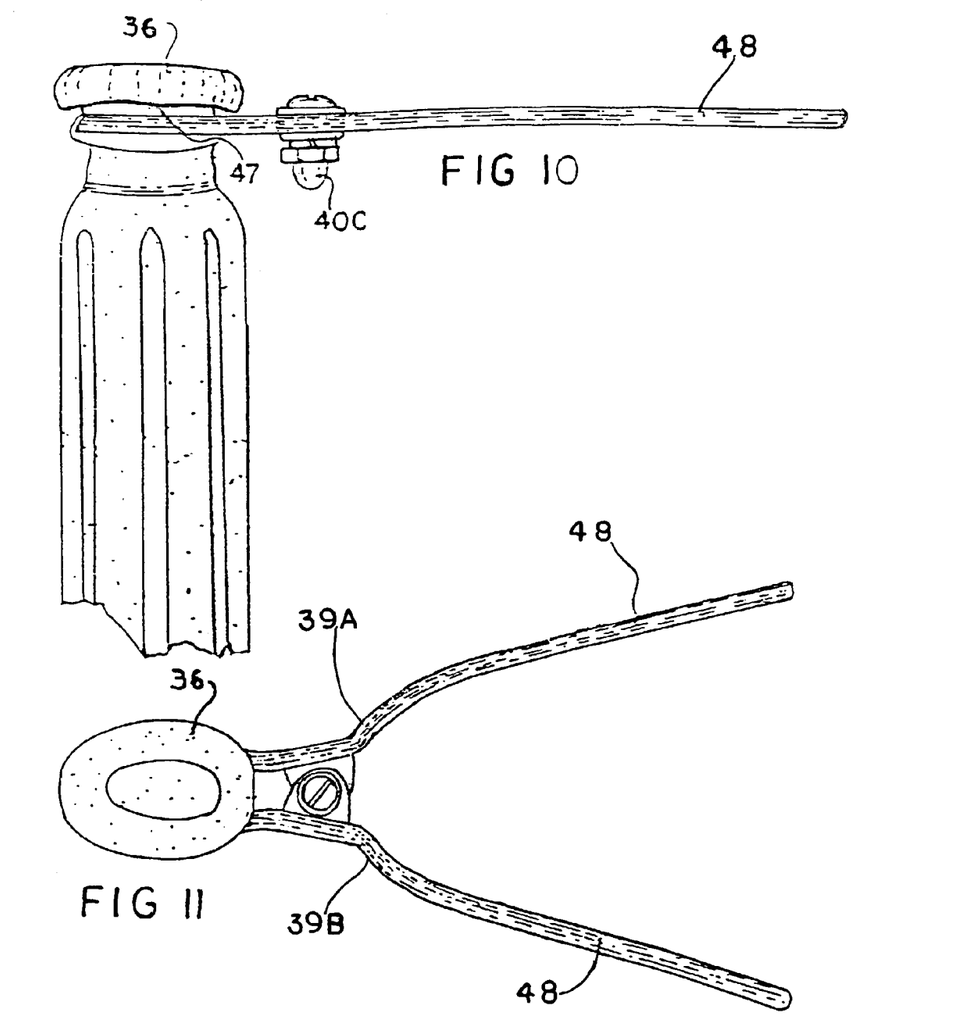
FIG. 10 is a side view of the applicator device of FIG. 6 with the rolled-up sheath pulled down into the recessed hooks on the two jaws.
FIG. 11 is a top view of the device and catheter as shown in FIG. 10 showing the rolled-up sheath around the jaws with the handles wide apart.

FIG. 11 shows a top view of sheath 36 in recessed ends 44, 45 and curved channels 47.

Figure 12:
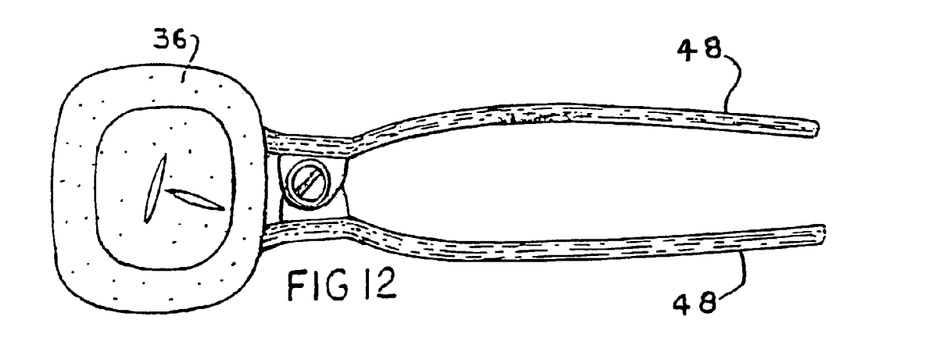
FIG. 12 is a top view of the device and catheter shown in FIG. 11 now with the handles closed together by hand pressure, and the rolled-up sheath spread wide open ready for applying it to a penis.

FIG. 12 shows the applicator handles 48 pressed together by hand, forcing the two jaws 43 to spread wide apart, thereby presenting the rolled-up part of the sheath 36 in the best possible form to be quickly and easily drawn up over a penis, either by a user or care-giver.

After the tip of the penis has been positioned close to the non-return valves, the sheath is rolled off the jaw ends 44 and 45 and curved channel 47, and the applicator device 38 removed.

Next, the sheath 36 is unrolled along the penis shaft, as far as it will go.

Finally, any air in the reservoir portion of the catheter is squeezed out of the condom catheter and its drain valve is closed.

Combined Apparatus

Figure 13:
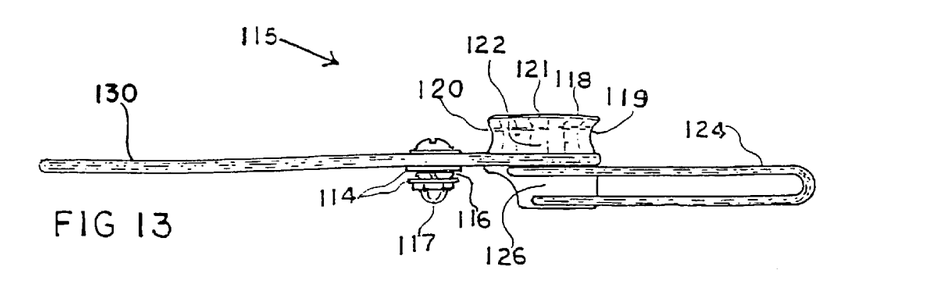
FIG. 13 is a side view of a one-piece roll-up applicator device according to the invention.
Figure 14:
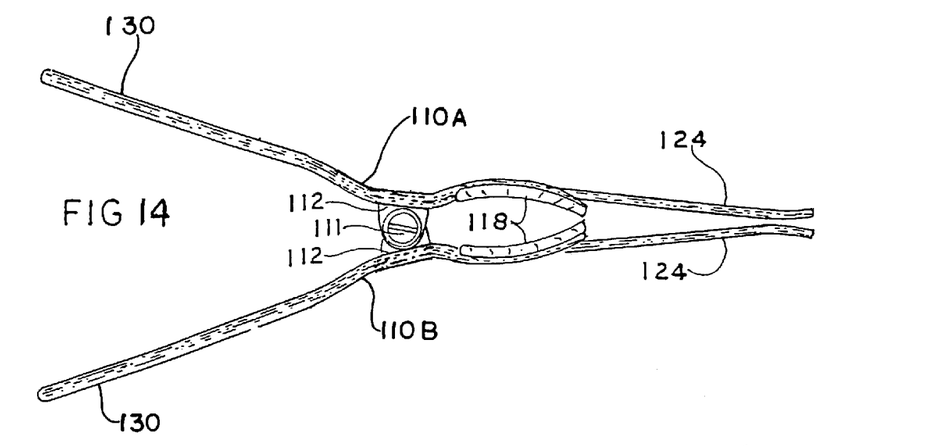
FIG. 14 is a top view of the device of FIG. 13.

FIGS. 13 and 14 show a combined roll-up applicator device 115 according to the invention. This device includes two opposing members 110A and 110B, which are made from 185 mm of 4 mm or 5 mm stainless steel rods, or any other suitable material. Members 110A and 110B are pivoted together by a pivot bolt 111 which passes through center holes in two friction discs 112 between members 110A and 110B. One friction plate 112 is attached to each member 110A or 110B by welding. Two flat washers 114, one spring washer 116 and one cap nut 117 are fitted onto bolt 111. The tightness of cap nut 117 on bolt 111 determines the resistance of movement between members 110A and 110B, which is necessary to hold jaws immobile together while the rolled-up sheath 128 is being transferred onto applicator jaws 118.

Each curved jaw 118 is made of 1 mm stainless steel sheet or other suitable material, and is permanently attached by welding or soldering or other suitable means to its respective member 110A or 110B. Each jaw 118 has two recessed ends 119 and 120 which form hooks. Top side 121 of each curved jaw 118 is bent outward to form a curved channel 122 between it and its respective member 110A and 110B. Those parts of members 110A and 110B remote from jaws 118 form handles 130.

Pivot bolt 111 is positioned between the two members 110A and 110B, so that when handles 130 are spread apart by hand, jaws 118 will close together; and when handles 130 are forced together by hand pressure, jaws 118 will spread apart with multiplied force.

Figure 15:
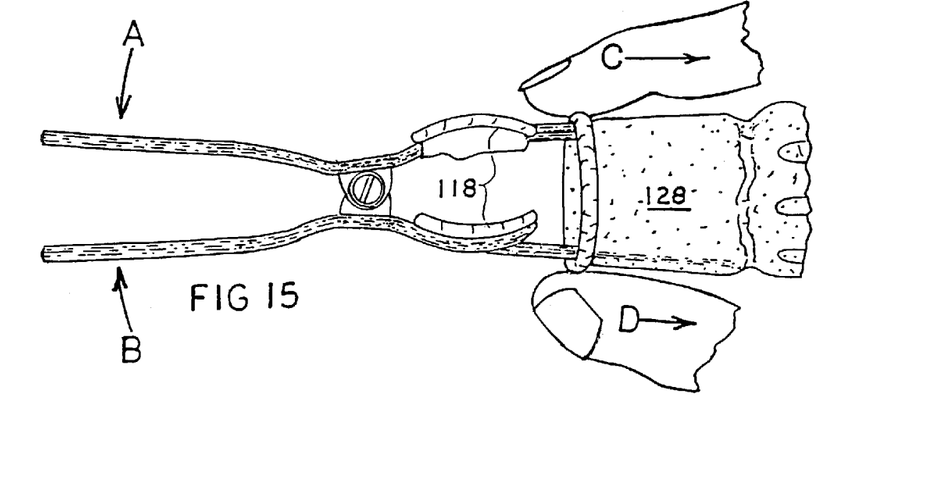
FIG. 15 is a top view of the device of FIG. 13 showing also a catheter partially rolled up on extended roll-up blades of the device.

Each curved jaw 118 has an integral flange 126, which protrudes below members 110A and 110B, as shown in FIG. 13. Two extension blades 124, made from 2.24 mm stainless steel wire are provided, each being welded or soldered to one of the flanges 126. When extension blades 124 are closed as shown in FIG. 14, they can both be inserted into condom catheter sheath 128 as shown in FIG. 15. When hand pressure is applied in the direction of arrows A and B, the two extended blades 124 stretch sheath 128 to form a rectangular tube. Sheath 128 can then be easily rolled down by the finger and thumb of the other hand in the direction of arrows C and D.

Figure 16:
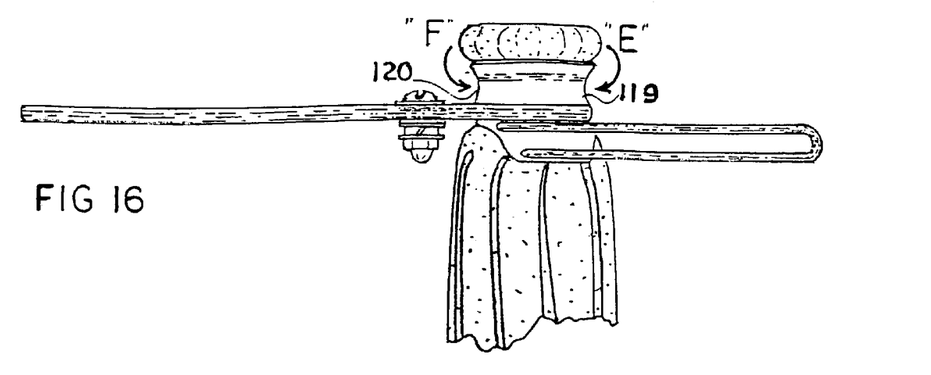
FIG. 16 is a side view showing the device of FIG. 13, clamped around a rolled-up catheter.

When rolling down is completed and the sheath 128 is freed from extension blades 124, the two curved jaws 118 are then positioned around the neck of the condom catheter and close to the rolled-up sheath 128, as shown in FIG. 16. The rolled-up part of sheath 128 is then transferred to the applicator jaws 118.

Figure 17:
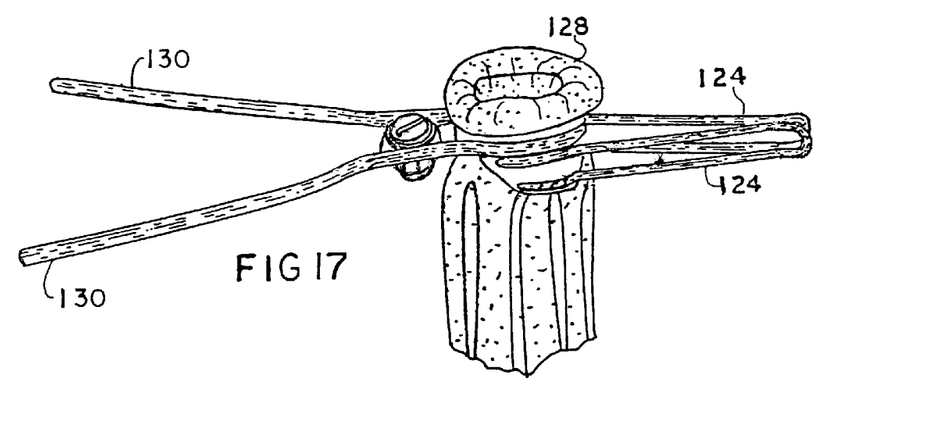
FIG. 17 is an elevated side perspective view showing the rolled-up sheath of the catheter fitted down around the jaws of the device of FIG. 13.

Arrows E and F, FIG. 16, indicate the direction and sequence by which the rolled up sheath 128 is pulled down by the fingers, first into recessed jaw end 119 near arrow E where it can be held in place by the thumb. Then the rolled-up sheath 128 is stretched into recessed jaw end 120 near arrow F. The remainder of the rolled-up sheath 128 will automatically accommodate itself into both curved channels 122, as shown in FIG. 17.

Figure 18:
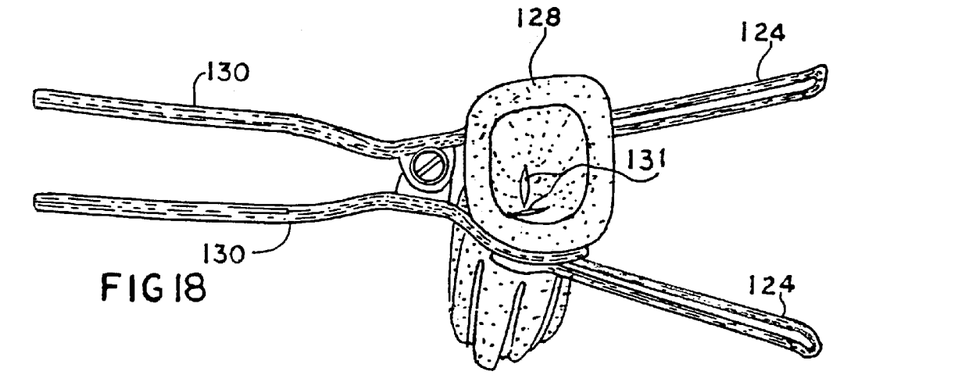
FIG. 18 is an elevated perspective view of FIG. 17, now with the handles closed together by hand pressure, and the rolled-up sheath spread wide open ready for applying it to the penis.

FIG. 18 shows the applicator side members 10A and 10B pressed together by hand, forcing jaws 118 to spread wide apart, thereby stretching and presenting the rolled-up sheath in the best possible form to be quickly and easily drawn up over a penis, while at the same time allowing the tip of the penis to come into contact with non-return valves 130 at the base of the sheath; by this means, application either by a user or a care-giver is facilitated.

After the tip of the penis has been positioned close to non-return valves 131, the sheath 128 is rolled off the jaw ends 119 and 120 and curved channels 122 and the applicator device 115 is removed.

Next, the sheath 128 is unrolled along the penis shaft as far as it will go.

Finally, any air is squeezed out of the reservoir portion of the condom catheter and the drain valve closed.

Thus the reader will see that simple devices and a method have been provided which enable rapid and convenient fitting of a condom-style catheter to a penis, by a user of the catheter or a caregiver.

It will of course be understood that many variations may be made to the devices described herein without departing from the spirit and scope of the invention.

What is claimed is:

1. Apparatus for fitting a condom-style catheter to a penis of a user, including at least two jaw members and movement means for moving said jaw members towards and away from each other, wherein:

said jaw members are adapted, in a first position relative to each other, to surround a first portion of said catheter and to retain against external surfaces of said jaws a toroidal roll formed of a rolled-up open-ended end portion of said catheter adjoining said first portion;

said movement means is operable by a user to move said jaw members outwardly to a second position relative to each other wherein said toroidal roll and a wall of said first portion of said catheter between said jaw members are distended to form an opening of a size and shape suitable to admit placement of an end of a penis therein;

said movement means is operable by a user to move said jaw members inwardly from said second position to a position in which said catheter is located on said penis and said toroidal roll is positioned for unrolling from said jaw members and thereafter along said penis by a user, so that said penis is located within said catheter; and said jaw members flare outwardly in a direction which in use of said apparatus lies along said penis whereby to aid retention of said toroidal roll on said jaw members.

2. Apparatus according to claim 1 wherein said jaw members are generally arcuate and in said second position relative to each other at least partially define a closed curve shaped and sized for passage therethrough of at least said end of said penis with clearance between said penis and said jaw members.

3. Apparatus according to claim 1 wherein ends of said jaw members have rounded projections to aid retention of said toroidal roll on said jaw members.

4. Apparatus according to claim 1 having two said jaw members and wherein said movement means includes two elongate members pivotally mounted to each other at a point partway along each said elongate member, each said jaw member is mounted on one of said elongate members in a position mutually opposing the other said jaw member, and a section of each elongate member on a side of the pivot opposite the jaw member thereon is adapted to serve as a handle.

5. Apparatus according to claim 4 wherein each said elongate member has an elongate extension and said extensions are adapted to be inserted together by a user into said end portion of said catheter and urged outwardly against an interior surface of said end portion by rotation of said elongate members about said pivot by a user, thereby to serve together as a former along which said end portion can be rolled by a user to form said toroidal roll.

6. Apparatus according to claim 5 wherein said extensions are so located on said elongate members that said extensions when within said end portion move outwardly within said end portion when those parts of said elongate members adapted to serve as handles are pushed towards each other by a user.

7. A pair of tools for fitting a condom-style catheter to a penis of a user including a first tool for forming an open-ended end portion of said catheter into a toroidal roll thereby to prepare said catheter for fitting to said penis, and a second tool according to claim 1.

8. A method for fitting a condom-style catheter to a penis using apparatus according to claim 1, the method including the steps of:

inserting at least one elongate object into an open end of said catheter;

rolling a portion of said catheter along said object to form said portion of said catheter into a toroidal roll;

positioning said jaw members around an unrolled portion of said catheter adjacent to said toroidal roll;

further rolling said catheter over said jaw members so that said toroidal roll is retained on said jaw members and said unrolled portion of said catheter is between said jaw members;

moving said jaw members apart from each other so that an opening bounded by said toroidal roll and a wall of said unrolled portion of said catheter between said jaw members is increased in size;

placing said penis in said opening; and unrolling said toroidal roll from said jaw members and thereafter along said penis, whereby to enclose said penis in said catheter.

9. A method according to claim 8 wherein a plurality of said elongate objects is inserted into said catheter and including the step of moving said elongate objects apart from each other within said catheter before rolling of said catheter therealong.

10. A method according to claim 8 including the step of withdrawing said at least one elongate object from said catheter after formation of said toroidal roll and before rolling of said toroidal roll onto said jaw members.

It is noted that this amendment is entered to correct a minor grammatical error and to provide clearer antecedent basis for the at least one elongate object. It is not intended to in any way meant to alter the substantive scope of the claim.

11. A method according to claim 8 including the step of moving said jaw members towards each other between the steps of placing said penis is in said opening and of unrolling said toroidal roll from said jaw members.

12. A method according to claim 8 wherein said jaw members are moved towards and away from each other along defined paths.

13. Apparatus for use in rolling an open-ended portion of a condom-style catheter into a toroidal roll, including two elongate arms pivotally secured to each other in generally "V" shaped arrangement with an angle between said arms being variable by pivoting, said arms being adapted to be inserted together by a user into said end portion of said catheter and urged outwardly against an interior surface of said end portion by pivoting of said arms, thereby to serve together as a former along which said end portion can be rolled by a user to form said toroidal roll, wherein said arms are extensions of ends of a helical spring arranged to urge said arms apart, said arms having to be pushed together by a user to enter said end portion of said catheter.

14. Apparatus according to claim 13 further including means for limiting said angle between the arms to a maximum value.

* * * * *